United States Patent [19]

Koro

[11] Patent Number: 4,653,022

[45] Date of Patent: Mar. 24, 1987

[54] PORTABLE ELECTROCARDIOGRAM STORING APPARATUS

[75] Inventor: Tsuneo Koro, Tokyo, Japan

[73] Assignee: Kabushiki Kaisha Tatebe Seishudo, Tokyo, Japan

[21] Appl. No.: 653,022

[22] Filed: Sep. 21, 1984

[30] Foreign Application Priority Data

Aug. 9, 1984 [JP] Japan .............................. 59-166956

[51] Int. Cl.[4] .......................... G06F 3/05; A61B 5/04
[52] U.S. Cl. .................................. 364/900; 128/709; 128/696
[58] Field of Search ... 364/200 MS File, 900 MS File, 364/300 MS; 128/695-711 MS

[56] References Cited

U.S. PATENT DOCUMENTS

| | | | |
|---|---|---|---|
| 4,422,081 | 12/1983 | Woods | 128/710 |
| 4,457,315 | 7/1984 | Bennish | 128/704 |
| 4,513,294 | 4/1985 | Anderson et al. | 128/710 |
| 4,519,398 | 5/1985 | Lisiecki | 128/710 |

FOREIGN PATENT DOCUMENTS 2649506 3/1978 Fed. Rep. of Germany ...... 128/710

OTHER PUBLICATIONS

*MBEC*, "Microprocessor Heart Rate Histogram Recorder for Ambulatory Monitoring of Daily Physical Activity", 5/81, pp. 367-369.

*Primary Examiner*—James D. Thomas
*Assistant Examiner*—C. H. Lynt
*Attorney, Agent, or Firm*—Stevens, Davis, Miller & Mosher

[57] ABSTRACT

A portable electrocardiogram storing apparatus has an electrocardiogram amplifier, an A/D converter for sampling the amplifier output and converting it into a digital signal, a patient actuatable switch, a plurality of electrocardiogram memories, and means for selecting one of the memories for storing the digital signal when the switch is actuated. A time memory is also provided for storing a time when the apparatus is set, and a timer measures a lapse time after the setting. A selected electrocardiogram memory also stores the content of the timer at the time a respective digital signal is stored therein.

4 Claims, 2 Drawing Figures

PORTABLE ELECTROCARDIOGRAM STORING APPARATUS

BACKGROUND OF THE INVENTION

1. Technical Field

The present invention relates to a portable electrocardiogram storing apparatus, and more particularly it relates to an electrocardiogram storing apparatus which is compact and light in weight and can store in IC (integrated circuit) memories not only electrocardiograms but also the time when the electrocardiograms are recorded.

2. Prior Art

Portable electrocardiogram storing apparatus provided with IC memories are carried by patients suffering from abnormalities of the heart, and more particularly by those patients who sometimes suffer from abnormalities of the heart in daily life but do not always show the symptoms, that is, patients suspected of a temporary arrhythmia. Upon occurrence of a subjective symptom the patient depresses a push button switch of the apparatus, which then stores the electrocardiograms during the period before and after, e.g., 40 seconds before and 20 seconds after the depression of the push button switch.

Since the apparatus is intended for use with patients whose abnormalities of the heart cannot be predicted, it has the capability of storing electrocardiogram several (e.g., five) times during a predetermined period (e.g., a week). However, if the derivation of information about the time at which the respective electrocardiograms were recorded is based upon the memory of the patient, it is difficult to assure its accuracy. Thus, it is difficult to obtain correct information on the relation between, on the one hand, each electrocardiogram, and, on the other hand, what the patient was doing, and/or what kind of symptoms the patient was suffering from when the recording was made.

Another consideration is the size and weight of the apparatus. Once the portable electrocardiogram storing apparatus is carried by the patient, it is continued to be carried until the storing of all electrocardiograms is completed or the predetermined time (e.g., a week) expires. It is therefore important to make the overall apparatus as small and as light as possible. For this to be realized, it is necessary to reduce the weight and volume of circuit components of the apparatus, and it is necessary to minimize the current consumption required for storing electrocardiograms. Further, it is necessary to minimize the current consumption which is required for storing and counting the time, so that a power source which is light in weight and small in volume suffices.

SUMMARY OF THE INVENTION

It is an object of the present invention to provide a portable electrocardiogram storing apparatus which can store the time when an electrocardiogram is stored, and which is light in weight and small in volume.

The portable electrocardiogram storing apparatus according to the present invention is provided with a time memory for storing the time when the apparatus is set, and a timer for measuring or registering a lapse time after the setting of the apparatus. The content of the timer at the time when the electrocardiogram is stored is also stored in the memory storing the electrocardiogram. Thus, information on the time when the electrocardiogram is stored can be obtained from the content of the timer stored and the content of the time memory.

DETAILED DESCRIPTION OF THE PREFERRED EMBODIMENTS

Figure 1:
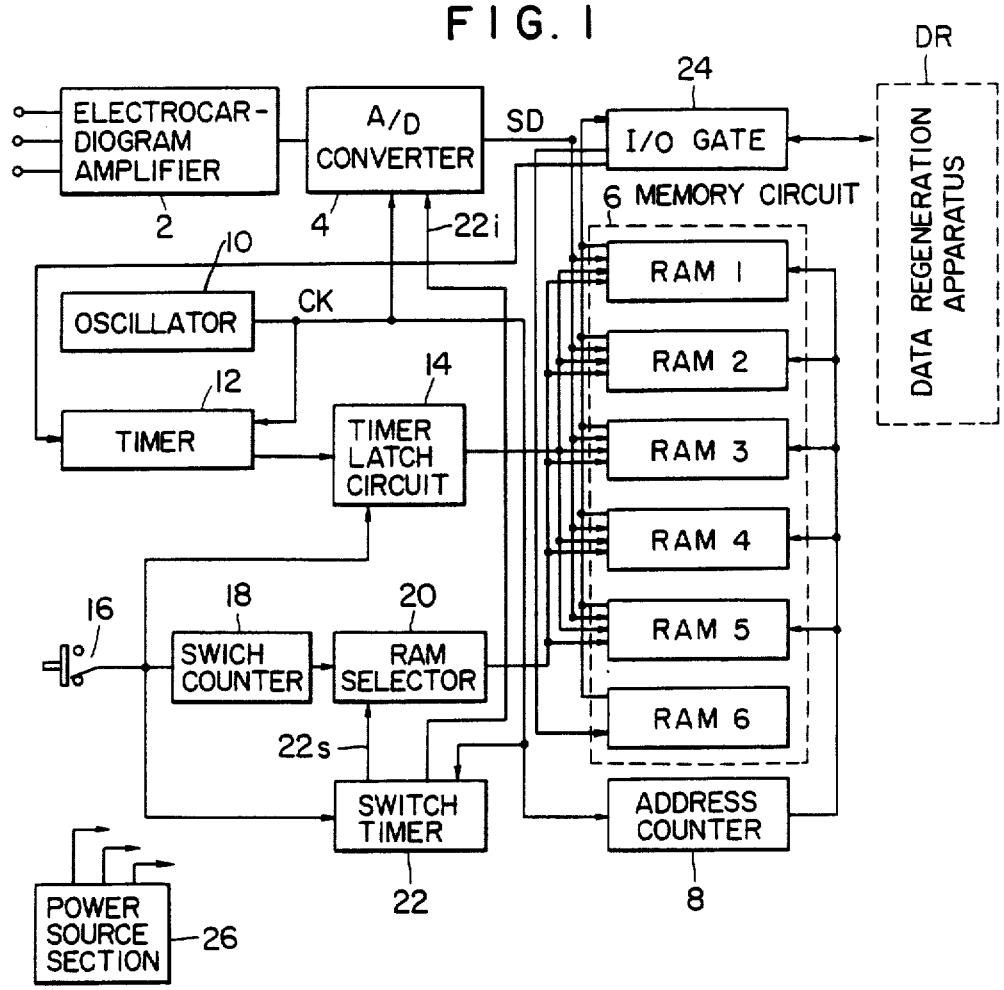
FIG. 1 is a block diagram showing a portable electrocardiogram storing apparatus according to one embodiment of the present invention.

FIG. 1 shows a schematic circuit block diagram of a portable electrocardiogram storing apparatus according to the present invention.

An electrocardiogram amplifier 2 amplifies, when it is connected to electrocardiogram electrodes attached to a living body, electromotive forces resulting from the heartbeats of the living body. The amplifier 2 comprises a buffer amplifier stage for amplifying the respective signals from the electrodes, and a differential amplifier stage for receiving the outputs from the buffer amplifier stage.

An A/D (analog-digital) converter 4 is fed with an analog signal from the electrocardiogram amplifier, and quantizes the analog signal every predetermined sampling interval, e.g. 10 m sec, into 256 values, and generates a digital signal of 8 bits.

A memory circuit 6 comprises six memory units, random access memory units RAM 1 through RAM 6. Among them RAM 1 through RAM 5 each have a capacity for storing not only the data representing sample values obtained every sampling interval (10 m sec) for one minute, but also a lapse time data described hereinafter and any attendant data whose storage may be desired. RAM 6 stores the year, month, day, hour, and minute (hereinafter referred to simply as time) when the apparatus is set. The information on the time is supplied from a data regeneration apparatus DR while the present apparatus is connected to the regeneration apparatus DR.

An address counter 8 is a counter for sequentially and cyclically designating a storage address (each address is composed of 1 byte) in RAM 1 through RAM 5 for each sample value data, and increments the address value by one every time it receives a clock pulse from an oscillator 10.

The oscillator 10 generates every sampling interval a clock pulse, by which the timing of sampling by the A/D converter 4 and the data writing by RAM 1 to RAM 5 are controlled.

A timer 12, formed, for example, of a counter, measures or registers the length of time or "lapse time" after the setting of the present apparatus, and for this purpose, it counts the clock pulses from the oscillator 10.

A timer latch circuit 14 is a circuit for latching the content of the timer 12 when a push button switch 16 described later is depressed.

The push button switch 16 is operable by the patient, and is operated or actuated when the storing of the electrocardiograms is required, for example when the subjective symptoms occurs.

A switch counter 18 is a counter for counting the number of operations or depressions of the push button switch. The content thereof is set at "1" when the present apparatus is set, and thereafter the content is incremented by one every time the switch is operated.

In response to the count value of the switch counter 18, and also on condition that a signal 22s from a switch timer 22 which will be described later is received, a RAM selector 20 changes its selection among RAM 1 through RAM 5. When the count value of the counter 18 is "1", the RAM selector 20 selects RAM 1. After that, the RAM selector 20 selects in turn RAM 2, RAM 3, RAM 4, and RAM 5 as the count value of the counter 18 increases and as the signal 22s is subsequently supplied. If the count value of the switch counter 18 increases further, the RAM selector 20 selects none of RAM 1 through RAM 5. The selection of RAM 1 through RAM 5 by the RAM selector 20 determines which RAM should store the sample data from the A/D converter.

A switch timer 22 measures the length of time after the push button switch 16 is depressed. To this end, it receives and counts the clock pulses from the oscillator 10. For 20 seconds after the switch 16 is operated, the sample data SD from the A/D converter 4 are successively stored at the respective addresses of the RAM being selected by the RAM selector 20. Upon expiration of the 20 seconds, the storing operation of the sample data SD is suspended. Thereafter, data having all the bits at "H" level, are successively written at the respective designated addresses of the selected RAM for a predetermined time, i.e., for a predetermined number of writing operations to form a header code. Then, a lapse time data which is latched at the timer latch circuit 14 is written in the selected RAM at the succeeding addresses. After this, the switch timer 22 supplies a signal 22s to the RAM selector 20, which, in response to the signal 22s, selects another RAM (e.g., RAM 2) different from the one (e.g., RAM 1) having been selected up to then.

An I/O (input/output) gate 24 is a bi-directional gate, and is used when the data stored by the present apparatus is connected to a data regeneration apparatus DR provided at a hospital or the like, and for setting the present apparatus at an initial condition or for collection or regeneration of data.

A power source section 26 supplies a power to various circuit components, and comprises, for example, mercury cells.

The operation of the apparatus described above will now be explained.

The present apparatus is connected, prior to being delivered to a patient, to a data regeneration apparatus DR at a hospital or the like for initial setting. This initial setting includes writing in the RAM 6 the information indicating the time at which the initial setting is done. In addition, the timer 12, counter 18, timer 22, RAM selector 20, and address counter 8 are all set at their respective initial values. Upon the initialization, the timer 12 starts to measure the time (a lapse time after the initialization).

The sample data SD successively appear at the output of the A/D converter 4, and each of the data is written into the RAM (first, RAM 1) being selected by the RAM selector 20 at the address being designated by the address counter 8. The address counter 8, in response to the clock pulse CK from the oscillator 10, increments the address value successively until it reaches the maximum value (the same for all of RAM 1 through RAM 5) of the RAM address. After that, the counter 8 returns to the minimum value of the address, and thereafter repeats the above counting operation. Thus, the sampling data SD is written cyclically into the RAM being selected. As a result, after the sampling data SD is written into all of the addresses of the RAM selected, the oldest data is erased and the latest data is stored at the address where the oldest data has been stored. Thus, a predetermined number (number of addresses of the RAM) of latest data continue to be retained.

When the push button switch 16 is depressed e.g., for the reason that the patient has suffered from an abnormality, the content of the timer 12 is latched at the timer latch circuit 14, the count value of the switch counter 18 is incremented by one, and the switch timer 22 starts to measure the time. And, for 20 seconds thereafter, writing the sample data SD is continued. After this, an ordinary operation of the A/D converter 4 is inhibited by a signal 22i for a predetermined time period, such as 640 m sec. Thereafter, the content of the timer latch circuit 14 is written in for a predetermined time, such as 320 m sec. As a result, a memory of a format shown in FIG. 2 results, in the selected RAM (RAM 1). Though the sequence of the storage of each data is fixed, the particular locations of storage of the respective data are not fixed. Upon completion of writing-in of the content of the timer latch circuit 14, the RAM selector 20 selects a different RAM (RAM 2). Then, the writing-in of the sample data SD into the newly selected RAM (RAM 2) starts. Subsequently similar operations are repeated.

Figure 2:
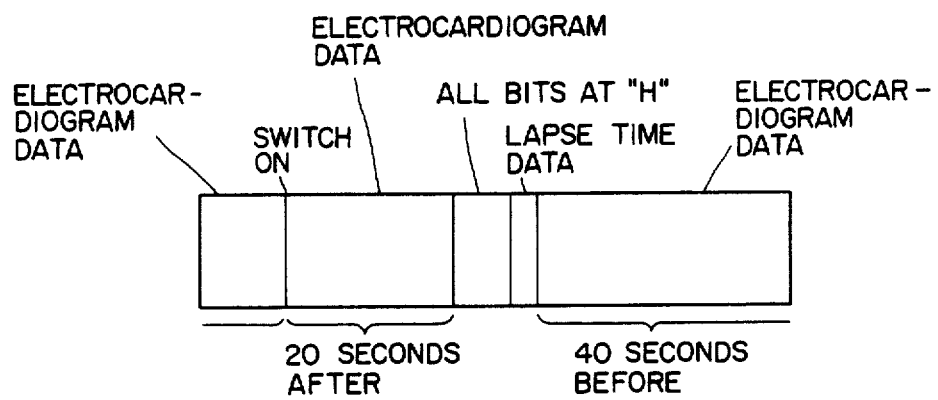
FIG. 2 is a format of the stored content of RAM 1 shown in FIG. 1.

After the switch has been depressed five times, and the data similar to that shown in FIG. 2 have been stored in the five RAMs (RAM 1 through RAM 5), the subsequent data are not written in any one of RAM 1 through RAM 5.

The regeneration or collection of data is carried out by connecting the I/O gate 24 to the data regeneration apparatus DR. By doing so, not only can each stored electrocardiogram (40 seconds before and 20 seconds after the actuation of the switch) be read out, but also a data representative of the time when the switch was actuated can be obtained from the content of the lapse time data of each RAM and the time data of RAM 6 at the setting of the apparatus.

Since each data within RAM 1 through RAM 5 has a format described above, it is required to locate the beginning of the lapse time data. For this purpose, when or after data in RAM 1 through RAM 5 are transferred to the regeneration apparatus DR, the location where bytes having all bits at "H" level continue to appear for predetermined times (64 times corresponding to 640 m sec), is sought out and the subsequent byte is recognized as the beginning of the lapse time data. And, the address which is located at the number of (i.e., 32) bytes corresponding to the predetermined time period (320 m sec) thereafter is recognized as the beginning of the electrocardiogram data.

In the embodiment described, the content of the timer 12 at the time of actuation of the switch 16 is latched in the timer latch circuit 14 and is stored in RAM 1 through RAM 5. But time other than the time of actuation of the switch 16, such as the content of the timer 12 at the time of 20 seconds after the actuation of the switch 16, may be stored in RAM 1 through RAM 5. This is because what is essential is that information of the time relating to the storage of electrocardiogram can be obtained.

Furthermore, the arrangement may be such that if the switch 16 is actuated more than once within a predetermined time period (for example, 60 seconds), the actuation other than the first actuation is ignored.

Moreover, each of RAM 1 through RAM 5 has been described as storing only the electrocardiogram data and the lapse time data. But where it is desired to store other data as well, such other data can also be stored. For example, upon expiration of a predetermined time (for example, 20 seconds) after actuation of the switch 16, bytes having all the bits at "H" level may be written continuously for a predetermined time period (e.g., 640 m sec), and subsequently the lapse time data and the above-mentioned other data may be written. The order in which the various data are written may be selected arbitrarily.

Furthermore, although the time memory has been used for storing the combination of year, month, day, hour, and minute, part only of the combination, day and hour only, or, conversely, in addition to the combination "second" may be stored in a suitably constructed time memory.

As will be understood from the above description, according to the present invention, time data indicative of the time when each electrocardiogram is stored can be obtained. In addition, such function can be realized by only adding principally a RAM (RAM 6) for storing the time when the apparatus is set, and the timer (timer 12) for measuring the lapse time after the setting of the apparatus. Thus, the apparatus can be made light in weight, and small in volume, and to consume little electric power.

What is claimed is:

1. A patient-borne electrocardiogram storing apparatus comprising:
    an electrocardiogram amplifier for amplifying an electrical signal from an electrocardiogram electrode;
    an analog-to-digital (A/D) converter for sampling the output from the electrocardiogram amplifier at a predetermined sampling interval and for converting it into a digital signal;
    a switch actuatable by a patient to initiate the storing of an electrocardiogram;
    a plurality of electrocardiogram memories which are selected in a predetermined order, said electrocardiogram memories being connected to said A/D converter, each of said electrocardiogram memories storing, when selected, said digital signal for a period occurring during a predetermined time before and a predetermined time after actuation of said switch;
    means responsive to actuation of said switch for selecting one of said electrocardiogram memories in accordance with said order to store said digital signal;
    a reference time memory for storing a reference time which is externally set at a time when said apparatus is activated;
    a lapse time timer for measuring a lapse time after said activating time; and
    a switch timer for measuring the time after the actuation of said switch,
    a selected electrocardiogram memory also storing a predetermined header code, and the content of said lapse time timer, said switch timer, after a predetermined time expires after actuation of said switch, causing the writing of the header code and the content of said lapse time timer in the selected electrocardiogram memory in place of the digital signal from said A/D converter.

2. An apparatus according to claim 1, further comprising a timer latch circuit for latching the content of said lapse time timer when said switch is actuated, each of said electrocardiogram memories, when selected, storing the content of said lapse time timer latched by said timer latch circuit.

3. An apparatus according to claim 1, wherein said selecting means and switch timer operate so that said electrocardiogram memories are successively and cyclically selected, so that the digital signal from the A/D converter is successively written in the selected electrocardiogram memory before the actuation of said switch and until the expiration of said predetermined time after the actuation of said switch, and after the expiration of said predetermined time, said header code and the content of said lapse time timer are written in the selected electrocardiogram memory.

4. An apparatus according to claim 3, further comprising a timer latch circuit for latching the content of said lapse time timer when said switch is actuated, each of said electrocardiogram memories, when selected, storing the content of said lapse time timer latched by said timer latch circuit.

* * * * *